United States Patent [19]

Van Dooren et al.

[11] Patent Number: 4,849,356

[45] Date of Patent: Jul. 18, 1989

[54] FRUCTOSYL TRANSFERASE AND THE PREPARATION OF FRUCTOSE OLIGOMERS THEREWITH

[75] Inventors: Theodorus J. G. M. Van Dooren, Roermond; Johannes A. M. Van Balken, Susteren, both of Netherlands

[73] Assignee: Stamicarbon B.V., Geleen, Netherlands

[21] Appl. No.: 217,471

[22] Filed: Jul. 11, 1988

[30] Foreign Application Priority Data

Jul. 9, 1987 [NL] Netherlands .......................... 8701616

[51] Int. Cl.$^4$ ............................................... C12N 9/00
[52] U.S. Cl. ........................................ 435/183; 435/97; 435/101; 435/193
[58] Field of Search ................... 435/183, 193, 97, 101

[56] References Cited

U.S. PATENT DOCUMENTS

| | | | |
|---|---|---|---|
| 4,276,379 | 6/1981 | Hendy | 435/193 |
| 4,309,505 | 1/1982 | Smith | 435/193 |
| 4,423,150 | 12/1983 | Heady | 435/193 |
| 4,617,269 | 10/1986 | Rathbone | 435/193 |

*Primary Examiner*—Peter D. Rosenberg
*Attorney, Agent, or Firm*—Cushman, Darby & Cushman

[57] ABSTRACT

Process for preparing a fructosyl transferase enzyme preparation by cultivating an Aspergillus species and recovering from the culture a preparation having fructosyl transferase activity, wherein *Aspergillus phoenicis* is cultivated and the mycelium is recovered from the culture medium.

8 Claims, No Drawings

FRUCTOSYL TRANSFERASE AND THE PREPARATION OF FRUCTOSE OLIGOMERS THEREWITH

The invention relates to the preparation of fructosyl transferase from a culture of an Aspergillus species, to a fructosyl transferase enzyme preparation obtained therefrom and to the application thereof in the preparation of fructose oligomers the molecules of which are composed of one glucose unit and two or more fructose units.

Interest in such fructose oligomers has been increasing on account of their favorable properties as low-calorie and non-cariogenic sweeteners, which fructose oligomers otherwise possess the good properties of sucrose as described in GB-A-2,072,679 (corresponding with NL-A-81.01587) and DE-A-3,232,531. Such fructose oligomers can be processed also to form high-grade fructose syrups as described in U.S. Pat. Nos. 4,276,379; 4,423,150 and 4,317,880 (corresponding with NL-A-81.02642).

It is known from GB-A-2,072,679 and DE-A-3,232,531 that fructosyl transferase and fructosyl transferase enzyme preparations can be obtained in very different way, particularly from cultures of fungi, such as Aspergillus, Pennicillium, Fusarium, Gloesporium species, from cultures of yeasts, such as Saccharomyces, Rhodotorulla, Pichia, Hansenula, Candida, Aureobasidium species and also from some plants, such as Asparagus officinalis (asparagus) and *Helianthus tuberosus* (Jerusalem artichoke). In the examples of these patent publications the preparation is described of a fructosyl transferase enzyme preparation from a culture of *Aspergillus niger*, as well as the application of such enzyme preparation for preparing a low-cariogenic and low-calorie sweetener containing fructose oligomers. They do not mention whether, and if so to what extent, the enzyme preparations obtained with different microorganisms differ from each other.

It is known in the art that there may be considerable differences between enzyme preparations prepared with different microorganisms. There may also be distinct differences, however, between enzyme preparations prepared with a particular microorganism under different process conditions.

Fructosyl transferase or fructosyl transferase enzyme is understood to mean any enzyme catalyzing transfructosylation. Transfructosylation is understood to mean the transfer of a fructosyl group from a donor, for instance sucrose, to an acceptor, for instance sucrose, kestose, nystose, etc. The structures of the enzymes are not known.

In the culture from microorganisms fructosyl transferase is obtained in the form of a fructosyl transferase enzyme preparation, which is understood to mean any product exhibiting the desired enzymatic activity. An enzyme preparation mostly contains components that are inactive and may also contain components exhibiting a different enzymatic activity. Enzyme preparations may consist of live whole cells, dry cells, cell extracts, purified and concentrated preparations and concentrated preparations derived from cells and from culture media, etc.

Fructosyl transferase enzyme preparations mostly also have invertase activity and in some cases they are found also to have isomerase activity. The invertase activity is undesired because, as a consequence, owing to the split-up into glucose and fructose, a part of the sucrose is not available for the conversion into fructose oligomers.

It has now been found that a fructosyl transferase enzyme preparation with favorable properties can be prepared by cultivating the fungus *Aspergillus phoenicis* in a culture medium suitable for fungal cultures and recovering the mycelium from the culture medium.

It is known from EP-A-81.200.723 (corresponding with NL-A-80.03723) that from cultures of Aspergillus phoenicis inulinase enzyme preparations can be recovered. In the process the fungus is pre-cultivated on a customary substrate, which mostly contains inulin. The spores are harvested and transferred to a culture medium, which contains inulin also. After a proper period of incubation the culture medium contains inulinase. The inulinase turns out not be cell-bound and can be separated from the mycelium with the liquid phase.

According to the present invention fructosyl transferase can be prepared in a similar manner on a substrate which will now mostly contain sucrose. This fructosyl transferase is cell-hound and can be recovered by separating the mycelium from the liquid phase. If in the absence of sucrose any fructosyl transferase is formed at all, the amounts concerned are small. Good yields of fructosyl transferase are obtained by incorporating in the culture medium sucrose.

The fructosyl transferases obtained according to the invention can be classified as EC 2.4.1.99 according to 'Enzyme Nomenclature Recommendation 1984' of the International Union of Biochemistry.

Although it is in principle possible in the same Aspergillus phoenicis culture to prepare inulinase as well as fructosyl transferase and to recover from these an inulinase enzyme preparation as well as a fructosyl transferase enzyme preparation, preference should be given to explicitly aiming the culture at either the formation of inulinase or at the formation of fructosyl transferase as the occasion requires. The addition of insulin to the culture medium realizes the formation of inulinase, while the addition of sucrose to the culture medium realizes the formation of fructosyl transferase.

Within the scope of the present invention many variants are possible, which the person skilled in the art will be able to work out easily. Thus the cultivation can be started, for instance, under circumstances favorable for the formation of inulinase in a medium suited for that purpose. After a suitable period of time the inulinase-containing culture medium is separated from the mycelium, upon which the mycelium is further cultivated in another medium favorable for the formation of fructosyl transferase under circumstances favorable for that purpose. By incorporating in the culture medium sucrose as well as inulin the two enzymes can be obtained concurrently, but that is not the optimum process for either of the two enzymes, and that is why preference will generally be given to separate preparation processes. The culture is most preferably so carried out as to be aimed, from the beginning, at either the formation of inulinase or at the formation of fructosyl transferase. Of course, neither the invention nor the possible variations within the scope of the invention are limited to the embodiments set forth hereinbefore.

The object of the present process is to prepare fructosyl transferase. Therefore, sucrose will be incorporated in the culture medium, and the other cultivation conditions, too, will generally be so chosen as to come to an optimum fructosyl transferase formation process.

Particularly suited for the preparation of fructosyl transferase is *Aspergillus phoenicis* CBS 294.80, filed by the applicant with the Centraal Bureau voor Schimmelcultures at Baarn, or a mutant or variant thereof. For a description of Aspergillus phoenicis reference is made to 'The Genus Aspergillus' by K. B. Raper and D. I. Fennel (Baltimore 1965)

The microorganism to be used according to the present invention, the fungus Aspergillus phoenicis, preferably the *Aspergillus phoenicis* CBS 294.80 filed by applicant, or mutants or variants thereof, can be pre-cultivated on a customary substrate, for instance on a solid substrate sterilized for 30 minutes at 110° C., composed of 20 g agar, 100 g sucrose, 5 g $K_2HPO_4$, 1 g NaCl, 3 g yeast extract, 0.2 g $MgSO_4.7\ H_2O$, 0.1 g $FeSO_4.7\ H_2O$, 0.1 g $MnSO_4.4\ H_2O$ per litre water. The pH thereof is 6.8. Pre-cultivation takes place for at least 8 days at 28° C. The spores are harvested. A liquid substrate having the same composition as the solid substrate, but without agar, is grafted with the spores. The cultivation of mycelium is effected in the manner customary for that purpose. The cultivated mycelium can then be filtered off. The mycelium contains cell-bound fructosyl transferase and can be used as such for the transfructosylation of sucrose. The mycelium can also be treated, worked up or processed further. After filtering off and mostly after washing out, it may, for instance, be homogenized in a high-speed mixer.

It will be clear that the fungus *Aspergillus phoenicis* can be cultivated on any other suitable substrate in any other suitable manner. As stated hereinbefore, the formation of fructosyl transferase is promoted by sucrose in the culture media. The greatest effect is achieved by sucrose in the liquid substrate for the cultivation of the mycelium. It is desirable also, however, to cause the solid substrate for the cultivation of the spores to contain sucrose.

The present fructosyl transferases are found to cause the preparation of fructose oligomers from sucrose, which fructose oligomers consist of one glucose residue and two or more fructose residues, to proceed with good yields at a pH of between 5.5 and 9.5. The fructosyl transferase activity reaches its maximum value in the pH range of 7.0 to 9.5. The pH is preferably between 7.0 and 9.0. The invertase activity of fructosyl transferases that always occurs is found, while the pH increases, to decrease rapidly from a pH of 5.5 and at a pH of 7.0 to reach a low value, which continues to decrease steadily, albeit more slowly, with a further increase of the pH. In the pH range of 7.0 to 9.0 the ratio of the fructosyl transferase and invertase activities is high, which is highly desirable. For the sake of brevity, the various sugars will hereinafter be referred to by symbols. G then stands for glucose or a glucose residue and F for fructose or a fructose residue. GF represents sucrose and $GF_2$ a sugar composed of one glucose residue and two fructose residues, such as 1-kestose, 6-kestose, neokestose; $GF_3$ represents a sugar composed of one glucose residue and three fructose residues, such as nystose, etc.

It is very surprising indeed for the favorable range of activity of the present fructosyl transferase enzyme preparations to occur at such high pH values. The optimum activity of fructosyl transferases known so far occurs at pH values lower than 7.0.

According to US-A-4,317,880, in the transfructosylation with a fructosyl transferase enzyme preparation Fecovered from a culture of the yeast *Pullularia* pullulans the pH must be between 6.3 and 6.7. Cultures of yeasts are usually more difficult to be processed further than cultures of fungi, and the cultures of yeast in particular are more difficult to be filtered. The thermal stability of enzyme preparations derived from yeasts is lower, too, i.e. at rising temperatures the activity of such an enzyme preparation decreases sooner than the activity of enzyme preparations derived from fungi, and its total loss, too, is more rapid. This implies that enzyme preparations derived from fungi and notably the present fructosyl transferase enzyme preparations, which are derived from cultures of *Aspergillus phoenicis*, can be used at higher temperatures than enzyme preparations derived from yeasts, which has many advantages. In this respect the present enzyme preparations also distinguish themselves favourably from fructosyl transferases derived from other fungi, albeit in a less distinct measure than from preparations derived from yeasts.

JP-A 85-41497 describes the preparation of fructosyl transferases in a culture of a yeast of the genus Aureobasidium and the transfructosylation at a pH of 5.0 to 6.0 with an enzyme preparation thus obtained.

According to GB-A-2,072,679, in the transfructosylation the pH must be between 4.0 and 7.0.

In US-A-4,276,379 and US-A-4,423,150 no optimum pH is mentioned, but all transfructosylations have been carried out at a pH of 5.5.

As stated hereinbefore, the present fructosyl transferases distinguish themselves from other known fructosyl transferases derived from fungal cultures also by an improved thermal stability, which means that at rising temperatures the activity of the present fructosyl proceeds more slowly than with other fructosyl tranferases. At a certain temperature the activity of the present fructosyl transferases is more stable than the activity of fructosyl transferases known in the art. The optimum temperature for preparing fructose oligomers from sucrose is higher. The optimum temperatures for the transfructosylation with the present fructosyl transferase range from 55° to 65° C.. Therefore, with a proper choice of the process conditions, which can be determined easily by experiment, the transfructosylation can be carried out at such temperatures that hardly any or no infection of the reaction mixture can occur any more. This is a very great advantage, for it cannot be achieved with the enzyme preparations known in the art, or at temperatures at which infection can be effectively countered there will be such a rapid decrease of the activity that the process is no longer economically feasible. Since systems known in the art must be used at lower temperatures, infection of reaction mixtures containing sucrose and enzyme preparations cannot be, or can hardly be prevented or countered effectively. The almost unavoidable infections of such reaction systems constitute a great disadvantage, of course, and it is therefore highly desirable if these can be prevented. All attempts to find a solution for this have failed so far. The present invention now also provides a solution for this problem. If so desired, the present fructosyl transferase enzyme preparations can be immobilized, too, resulting mostly in an increase of the optimum transfructosylation temperature. This may be important to further stabilize the activity at temperatures at which hardly any or no infection occurs any more, so that the decrease in activity will be slower still.

The immobilization of the present fructosyl transferases may be desirable also or in part for a variety of other purposes such as, for instance, the purpose of being capable of using the enzyme in a fixed or fluidized bed. The immobilization can be achieved according to techniques generally known in the art. In this connection reference is made to 'Immobilized Microbial Cells' by Ichiro Chibato and Lemuel B. Wingard Jr. (Academic Press 1983) and to the general article by Howard H. Weetall and Wayne H. Pitcher Jr. in Science 232 1396-1403 (986).

A maximum transfructosylation temperature is desirable also for obtaining a favorable viscosity of the usually rather highly concentrated sugar solutions. Accordingly, as the temperature rises, the often viscous solutions can be handled better and be filtered more easily thanks to the decrease in viscosity. Concentrated sugar solutions have been found to yield various advantages. For instance, the concentration of sucrose has been found to influence the fructosyl transferase activity. Favorable activities occur with sucrose concentrations ranging from 25 to 90% (wt) sucrose per litre solution. As stated hereinbefore, it is desirable for the ratio of the fructosyl transferase activity to the invertase activity to be as high as possible. The highest values of this ratio occur with sucrose concentrations ranging from 75 to 82.5% (wt/vol). Surprisingly, the thermal stability of the enzyme, too, has been found to he influenced hy the sucrose concentration, and the highest thermal stability is obtained with sucrose concentrations again ranging from 75 to 82.5% (wt), so that with these concentrations the highest temperatures can be applied.

Another favorable characteristic of the present fructosyl transferases is that in the transfructosylation 1-kestose ($GF_2$) and nystose ($GF_3$) are formed almost exclusively. $GF_4$ and higher oligomers cannot been demonstrated. Of the possible $GF_2$ isomers 1-kestose is formed and no 6-kestose and neokestose. The amount of glucose that is formed in the system in the transfructosylation process is minimized by the formation for the most part of kestose. Owing to the low invertase activity the inversion of sugar continues to be very low, resulting again in the formation of only a small amount of glucose. The end product contains relatively little glucose.

The sucrose to be used in the present process may be virtually pure sucrose in the form of beet or cane sugar, as well as a technical sugar-containing product, such as molasses, etc.

Although for the transfructosylation any sucrose-containing product can in principle be used, products with a high sucrose content without disturbing impurities will preferably be started from.

The invention is elucidated with the following examples without being limited by these.

The reaction mixtures obtained in the transfructosylation of sucrose have been analyzed by high-pressure liquid chromatography (HPLC).

The fructosyl transferase activity mentioned in the examples is expressed in micromoles ($\mu$mole) of fructose oligomers (here exclusively $GF_2$ and $GF_3$) formed per minute per g dry mycelium. The activity of the small amounts of invertase present is defined as the number of $\mu$moles of fructose formed per minute per g dry mycelium.

EXAMPLE 1

A culture medium of 100 g sucrose, 5 g $K_2HPO_4$, 3 g yeast extract, 1 g NaCl, 0.2 g $MgSO_4.7\ H_2O$, 0.1 g $FeSO_4.7\ H_2O$, 0.1 g $MnSO_4.4\ H_2O$ per litre solution was grafted with spores (final concentration about $10^8$ spores per litre) of Aspergillus phoenicis CBS 294.80. The fungus was cultivated in a reciprocal incubator for 2 days at 30° C. The mycelium was subsequently filtered off, washed with water and then it was ground in a Virtis mixer. To 100 ml of a 75% (wt/vol) sucrose solution, the pH of which had been set by means of a phosphate buffer at 8.0, 1 g wet (corresponding with about 0.28 g dry) mycelium was added. The solution was heated at 55° C. and stirred. After various reaction times samples were drawn from the solution, cooled and analyzed for fructose, glucose, sucrose, 1-kestose ($GF_2$) and nystose ($GF_3$). The results are summarized in table I.

TABLE I

| reaction time in hours | fructose g/100 ml | glucose g/100 ml | converted sucrose g/100 ml | 1-kestose ($GF_2$) g/100 ml | nystose ($GF_3$) g/100 ml |
|---|---|---|---|---|---|
| 1 | 0.4 | 3.5 | 11.6 | 5.2 | 1.7 |
| 4 | 1.0 | 10.0 | 34.5 | 18.1 | 4.7 |
| 8 | 1.7 | 15.8 | 53.2 | 28.2 | 7.5 |
| 12 | 2.3 | 18.4 | 60.8 | 31.7 | 8.6 |
| 18 | 2.9 | 20.2 | 65.6 | 28.2 | 13.3 |

The average FT activity for the first hour was 756, from hour 1 till hour 4 603, from hour 4 till hour 8 360 and from hour 8 till hour 12 128. The average FT/I ratio for the first hour was 7.5, from hour 1 till hour 4 7.8, from hour 4 till hour 8 6.4

EXAMPLE 2

Example 1 was repeated with the exception that the transfructosylation was carried out at 60° C.

The results are summarized in table II.

TABLE II

| reaction time in minutes | fructose g/100 ml | glucose g/100 ml | converted sucrose g/100 ml | 1-kestose ($GF_2$) g/100 ml | nystose ($GF_3$) g/100 ml |
|---|---|---|---|---|---|
| 15 | <0.2 | 2.3 | 8.8 | 6.1 | 0.1 |
| 30 | 0.25 | 3.8 | 13.7 | 9.3 | 0.3 |
| 60 | 0.5 | 6.2 | 22.5 | 15.1 | 0.7 |
| 120 | 0.8 | 10.0 | 35.0 | 21.7 | 2.8 |
| 180 | 1.0 | 12.1 | 42.5 | 25.7 | 3.5 |
| 240 | 1.2 | 13.7 | 47.5 | 28.2 | 4.5 |

The FT activity for the first 30 minutes is 2250, from 30-60 minutes 1440, from 60-120 minutes 950, from 120-180 minutes 550, from 180-240 minutes 390.

The average FT/I ratio for the first 30 minutes is 14.5, from 30-60 minutes 14, from 60-120 minutes 9.5, from 120-180 minutes 8.5 and from 180-240 minutes 5.4.

In a comparison with example 1, which was carried out at 55° C., the activity is found for the first hour to be more than twice as high and the FT/I ratio to be nearly twice as high.

We claim:

1. A process for preparing a fructosyl transferase enzyme preparation comprising the steps of:
   (a) cultivating *Aspergillus phoenicis* in a culture medium, the *Aspergillus phoenicis* forming mycelium; and
   (b) recovering said mycelium from the culture medium, said mycelium having fructosyl transferase activity, said preparation including said mycelium.

2. Process according to claim 1, wherein Aspergillus phoenicis CBS 294.80 or a mutant or variant thereof is cultivated and the mycelium is recovered.

3. Process according to claim 1, wherein the culture medium contains sucrose.

4. Process according to claim 1, wherein the mycelium is absorbed on resp. in, absorbed to, or otherwise bound to a solid carrier.

5. Process for preparing fructose oligomers, said oligomers comprising one glucose unit and at least two fructose units, by transfructosylation of sucrose using fructosyl transferase, wherein a fructosyl transferase enzyme preparation according to claim 1 is employed.

6. Process according to claim 5, wherein the transfructosylation is carried out in a solution with a pH of 5.5–9.5.

7. Process according to claim 6, wherein the transfructosylation is carried out in a solution with a pH of 7.0–9.0.

8. Fructosyl transferase enzyme preparation whose fructosyl transferase activity is pH dependent and has maximum activity in the pH range of 7.0 to 9.0.

* * * * *

UNITED STATES PATENT AND TRADEMARK OFFICE
CERTIFICATE OF CORRECTION

PATENT NO. : 4,849,356

DATED : July 18, 1989

INVENTOR(S) : Theodorus J.G.M. VAN DOOREN and Johannes A.M. VAN BALKEN

It is certified that error appears in the above-identified patent and that said Letters Patent is hereby corrected as shown below:

```
Column 1, line 26, please change "way" to --ways--;
column 2, line 22, please correct the spelling of "cell-bound";
column 2, line 39, please correct "insulin" to be --inulin--;
column 3, line 68, please correct the spelling of "recovered";
column 5, line 26, "he" should be --be--;
column 7, line 4, please correct "resp. in, absorbed to," to read
--resp. in, adsorbed to,--.
```

Signed and Sealed this

Fourteenth Day of August, 1990

Attest:

HARRY F. MANBECK, JR.

*Attesting Officer*      *Commissioner of Patents and Trademarks*